United States Patent [19]

Oloff et al.

[11] Patent Number: 4,653,509
[45] Date of Patent: Mar. 31, 1987

[54] GUIDED TREPHINE SAMPLES FOR SKELETAL BONE STUDIES

[75] Inventors: Clarence M. Oloff, Dayton, Ohio; Linda M. Hermann, Feasterville, Pa.; William G. Moss, Enon; Steven R. Sims, Dayton, both of Ohio

[73] Assignee: The United States of America as represented by the Secretary of the Air Force, Washington, D.C.

[21] Appl. No.: 751,393

[22] Filed: Jul. 3, 1985

[51] Int. Cl.[4] .......................................... A61B 10/00
[52] U.S. Cl. .................................... 128/749; 128/751; 128/754; 128/755; 128/303 B; 128/310
[58] Field of Search .................... 128/303 B, 310, 749, 128/751, 754, 755

[56] References Cited

U.S. PATENT DOCUMENTS

| | | | |
|---|---|---|---|
| 1,571,140 | 1/1926 | O'Connor . | |
| 2,245,350 | 6/1941 | Marshall | 33/189 |
| 2,426,535 | 10/1944 | Turkel | 128/754 |
| 2,740,406 | 7/1954 | Tofflemire | 128/310 |
| 3,073,310 | 1/1963 | Mocarski | 128/303 |
| 3,357,431 | 3/1965 | Newell | 128/303 B |
| 3,374,548 | 3/1968 | Romney | 33/174 |
| 3,508,552 | 4/1970 | Hainault | 128/303 |
| 3,512,519 | 5/1970 | Hall | 128/310 |
| 3,964,480 | 6/1976 | Froning | 128/303 B |
| 4,007,732 | 2/1977 | Kvavle et al. | 128/754 |

FOREIGN PATENT DOCUMENTS 683726  9/1979  U.S.S.R. ............................. 128/754

OTHER PUBLICATIONS

Robert D. Ray, "Needle Biopsy of the Lumbar Vertebral Bodies", The Journal of Bone and Joint Surgery, vol. 35-A, No. 3, Jul. 1953.
I. S. Fyfe et al., "Closed Vertebral Biopsy", The Journal of Bone and Joint Surgery, vol. 65-B, No. 2, Mar. 1983.

*Primary Examiner*—Kyle L. Howell
*Assistant Examiner*—Randy Citrin
*Attorney, Agent, or Firm*—Gerald B. Hollins; Donald J. Singer

[57] ABSTRACT

A bone biopsy arrangement especially suited for use in obtaining axial skeleton trephine samples from the spinal vertebra centrum of a living test specimen in a safe and rapid manner. The disclosed arrangement uses radiographic mapping, precise mechanical control of the trephine with an apparatus disclosed in detail, conventional trephine energizing and a test specimen such as a rhesus monkey. Improved quality plural samples from a single test subject that were heretofore considered too inaccessible and dangerous for practicality are achieved.

2 Claims, 3 Drawing Figures

GUIDED TREPHINE SAMPLES FOR SKELETAL BONE STUDIES

RIGHTS OF THE GOVERNMENT

The invention described herein may be manufactured and used by or for the Government of the United States for all governmental purposes without the payment of any royalty.

BACKGROUND OF THE INVENTION

This invention relates to the field of living specimen bone biopsy and to the trephine sampling of bone.

Trabecular bone found in the axial skeleton of animal and human test subjects is especially responsive to conditions of weightlessness, decreased usage, and physical exercise in anthropoid test subjects. Such bone is also of special interest in the diagnosis and treatment of certain disease processes. Since bone is living tissue and is being continuously remodeled throughout the life of a living specimen, changes in bone usage or loading are, for example, followed by confirming structural remodeling of the loaded bone wherein the remodeling follows the direction and functional stress applied by the loading. According to a generally accepted theory proposed by J. D. Wolff in Das Gesets der Transformation der Knochen, Berlin, A. Hirschwald, 1892, pp. 1-152, when the stresses applied to a weight-bearing living skeleton are changed or removed, such as through immobilization or gravity changes, directly responsive structural change or bone remodeling is expected. Since little is known of the physiology of bone remodeling under conditions of weightlessness and related mechanical stresses, the continued participation of human and animal test subjects in space efforts suggest a need for improved arrangements for studying bone remodeling.

The study and treatment of disease processes including the effects of bone tuberculosis, metabolic osteoporosis, disuse osteoporosis, (e.g., from prolonged bed confinement), syphilis, paraplegia, cast confinement, and other causes, serve also as a stimulus for continued study of bone remodeling and especially to bone degeneration processes.

Radiology, radiographic densitometry, and photon absorption spectrometry have been previously used in the analysis of bone with limited degrees of success—in view of the absence of quantitative information from such procedures. In sharp contrast of this limitation, however, a variety of reliable and accurate analytical techniques such as scanning electron microscopy, transmission electron microscopy, histomorphometry, after serial bone labeling, histochemistry, biochemistry, and mechanical strength tests are available for use in analyzing actual bone samples from a test subject.

The present invention provides an arrangement for obtaining desirable bone tissue samples from living animal or human test subjects which is both humane in that it is non-disabling and productive of only minimal and short duration discomfort for the test subject, and is also cost-efficient in permitting continued and repeated use of a single test subject for both prolonged and multiple studies.

Major additional considerations in obtaining axial skeleton bone biopsy samples include the location of the biopsy site, bones in the leg, for example, having heretofore been popular for such samples; and the obtaining of a sufficient quantity of undamaged specimen from an area representative of the conditions being studied. Trabecular bone, i.e., lattice organized crystalline bone, develops along the lines of greatest stress in the skeleton of an anthropoid and comprises the major weight bearing structural element in such organisms. A vertebral biopsy, especially a biopsy of the vertebral centrum portion has been found especially desirable for trabecular bone study in the case of anthropoids such as the rhesus monkey (macaca mulatta). Sampling accomplished in the easily accessible and structurally active spinal lumbar area of such test specimens is found to be particularly indicative of bone remodeling and other bone conditions.

The patent art includes several examples of bone sampling, skeletal measuring, and related procedures, this art includes the patent of R. H. Romney, U.S. Pat. No. 3,374,548, which described a stereotaxic system useful in tracing or following a pre-existing contour map in locating a drill bit precisely with respect to the skull of a test subject. The Romney apparatus includes a plurality of linear and angular adjustments capable of locating the drill bit or other cutting tool in most positions around the rigidily held skull of an anesthesized animal test subject. In the Romney apparatus the test subject is positioned on a stage 12 while a mensurative standard or map 45 is provided for use in locating and recording the positions of the drilling unit or an electrode about the skull of the test subject.

Other skull positioning instruments are shown in the patents of Z. R. Mocarski, U.S. Pat. No. 3,073,310, and H. Hainult, U.S. Pat. No. 3,508,552, and provide skull access for x-ray photograph and surgical purposes, respectively.

Positioning apparatus for other portions of the human anatomy are shown in the patents of M. F. O'Connor, U.S. Pat. No. 1,571,140, and G. R. Marshall, U.S. Pat. No. 2,245,350, which concern a chiropractic locating device and a lower spinal area hypodermic needle anesthetic administering apparatus, respectively.

While the above-identified patents indicate the use of mechanical aids in locating precise positions about a test subject to have been practiced for some time, none of these prior patents teach the use of a simple, reliable device for achieving fast, safe spinal vertebra trephine biopsy samples.

SUMMARY OF THE INVENTION

An object of the present invention is to provide a mechanical guidance arrangement for obtaining optimum bone biopsy trephine samples from a living test subject.

Another object of the invention is to provide an arrangement for safely securing high-quality trephine samples from the spinal vertebra of a living test subject.

Another object of the invention is to provide a bone remodeling study arrangement which is based on the acquisition of plural high-quality bone trephine samples from a single test subject.

Another object of the invention is to provide a new and safe arrangement for obtaining intersecting trephine samples from a single spinal vertebra.

Another object of the invention is to provide a bone remodeling study arrangement wherein the test subject can serve as its own control reference for successive testing.

Another object of the invention is to provide a bone biopsy arrangement which can be safely and practically used in the obtaining of plural samples from a test subject at one sample time.

Another object of the invention is to provide a bone biopsy trephine sampling arrangement capable of acquiring full vertebra diametered trephine samples.

Another object of the invention is to provide a bone biopsy trephine sampling arrangement wherein samples of sufficient size as to be undamaged during sample collection and preparation are obtainable.

Another object of the invention is to provide a bone biopsy arrangement which poses minimum risk to the living test specimen through the achievement of precise and accurate trephine guidance during the biopsy procedure.

Another object of the invention is to provide a trephine guidance apparatus which affords minimal complexity and clutter in the field of a specimen radiograph.

Another object of the invention is to provide a trephine biopsy guidance arrangement which employs easily portable apparatus readily attachable to a radiographic table or other surgery suite equipment.

Another object of the invention is to provide a trephine biopsy apparatus capable of implementing a trigonometrically computed trephine access path that is difficult of achievement with heretofore used apparatus procedures.

Another object of the invention is to provide a trephine biopsy arrangement having a compatibility with presently used apparatus such as test subject cradles and pneumatic drilling devices.

Additional objects and features of the invention will be understood from the following description and the accompanying drawings.

These and other objects of the invention are achieved by a trephine biopsy apparatus which includes a powered drilling tool having a rotationally driven chuck member, a horizontally disposed way member rigidly disposable above and laterally across the spinal axis of an anteriorly reposed test subject in selected vertical separation therefrom, a selectably positionable indexing member movably disposed on the way member and locatable within a vertically oriented plane radial of the test subject spinal axis with the lower end thereof in physical adjacency to the spinal process of the test subject, a selectably positionable tool platform member movably disposed on the way member and locatable at predetermined distances from the indexing member along the way member, a tool carriage member pivotally and slidably disposed on the platform member and pivotally constrainable in an angularly sloping plane radial of the test subject's spinal axis, the carriage member including receptacle means for retaining the powered drilling tool captive therein, and sliding means enabling radial movement of the drilling tool within the sloping radial plane with respect to the spinal axis, a hollow trephine cutter bit received in the chuck member, and measuring means disposed adjacent the movably and slidably disposed members for determining the location and movement extent of the trephine cutter bit with respect to the spinal axis.

DETAILED DESCRIPTION

Figure 1:
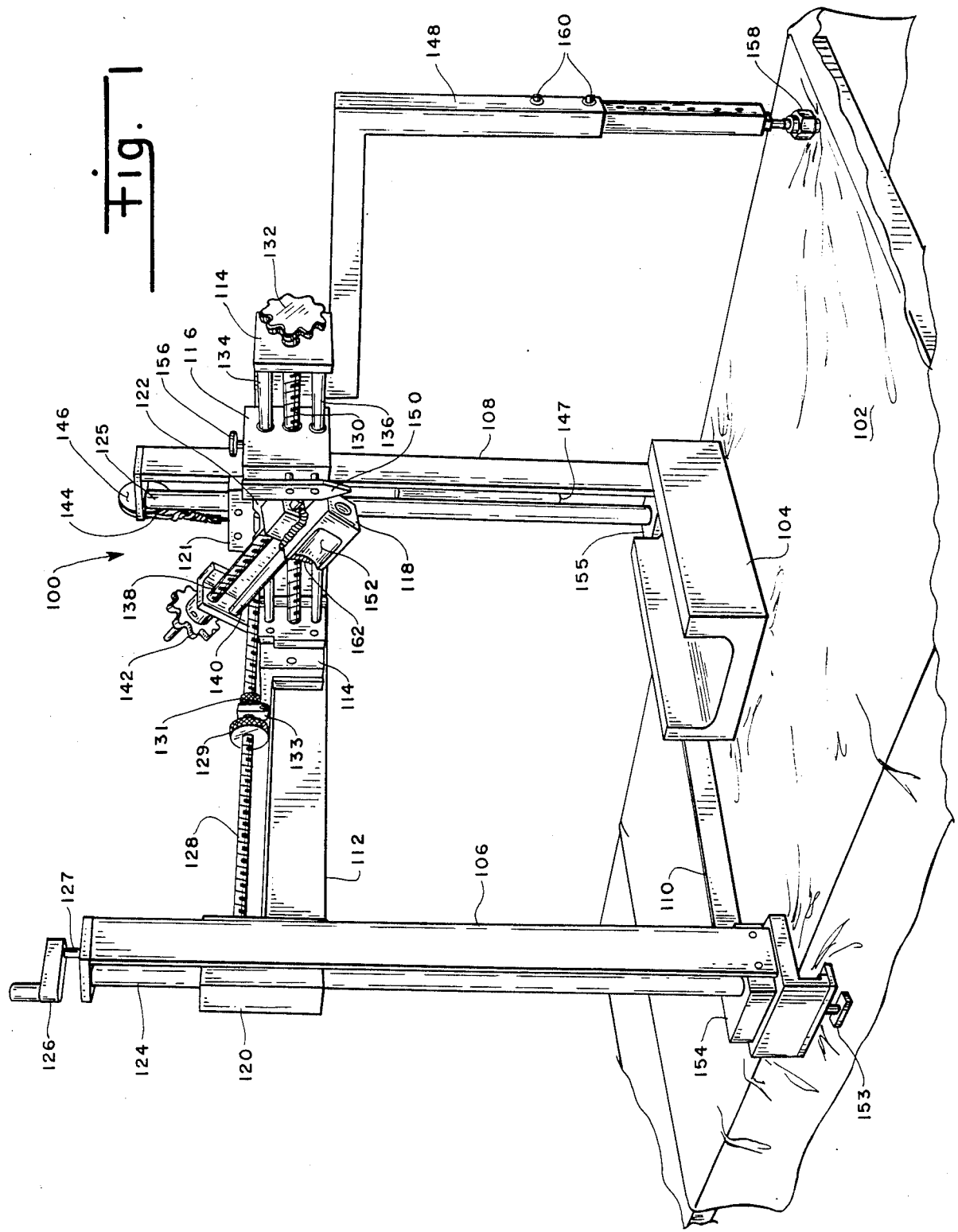
FIG. 1 is a perspective view of a trephine guidance apparatus made in accordance with the invention.

FIG. 1 of the drawings is a perspective view of a sample accessing apparatus usable in obtaining trabecular bone axial skeleton samples from the lumbar spinal vertebra centrum of a rhesus monkey or other test subject. As indicated earlier herein, with the aid of the FIG. 1 apparatus, such spinal vertebra bone samples are obtainable with negligible discomfort and minimal risk to a loving and valuable test specimen. With the aid of the FIG. 1 apparatus, a given test specimen can therefore provide numerous spinal vertebra samples while leading a normal active life; the samples thereby obtained also being of increased scientific interest in view of their source from a single living test specimen and their possible withdrawal over an extended time period.

The FIG. 1 sample accessing apparatus, 100, is shown in conjunction with a surgical table 102 and a test specimen surgical cradle 104. The accessing apparatus includes a pair of upright standard members 106 and 108 which are fixedly connected by a horizontally disposed lower connecting bar 110 at their lower extremity and by an upper movably disposed connecting bar 112. The upright standards 106 and 108 are mounted on a pair of foot members 154 and 155 having a recessed clamp area receivable on the table 102. The fixed connecting bar 110 is preferably attached to one side of the foot members 154 and 155, while the upright standards 106 and 108 are attached to the opposite side of the foot members. Each of the foot members 154 and 155 may include a pair of threaded clamping members 153 capable of forceful engagement with the lower side of the table 102.

Received on the upper, movably disposed, connecting bar 112 is a movable way member 114 which optionally may be supported at its outward end by a support leg member 148. The movable way member 114 is positionable along the upper connecting bar 112 and retainable in a selected position by means of a threaded lead screw member 128 on which is received a pair of threaded adjustment nuts 129 and 131 that engage with a portion 133 of the movable way member 114.

Movably mounted on the way member 114 in FIG. 1 is a selectably positionable tool platform member 122 which is movable in the left and right direction of FIG. 1 along a pair of slides or guide members 134 and 136. Movement and positioning of the tool platform member 122 along the way member 114 is controlled by a second threaded lead screw member 130 on which is received a thread engaging nut located within the tool platform member 122. Rotational movement of the threaded lead screw member and movement of the tool platform member 122 can be achieved by manual movement of the knob 132.

An additional selectably positioned member, the index assembly 116 is also movably disposed on the way member 114. The index assembly 116 is more clearly shown in FIGS. 2 and 3 of the drawings, and is retained in any selected position along the way member 114 and the guide members 134 and 136 by a knob and set screw 156. The index pointer 150 which is mounted on the index assembly 116 serves as a measurement reference point during use of the FIG. 1 apparatus, as is explained below.

Supported on the tool platform member 122 is a slidably mounted tool carriage member 118 which is disposed at a predetermined angle, near 30°, with respect to the movement direction of the tool platform member 122 along the guides 134 and 136. The tool carriage member 118 is movable along an angularly disposed slide or guide member 140 and is position controlled by a third threaded lead screw member 138 rotatably driven by a manually actuatable knob 142. As is more clearly shown in FIGS. 2 and 3 of the drawing, the lead screw member 138 passes through and is engaged by a portion of the tool carriage member 118. The tool carriage member 118 also includes a cavity receptacle 152 in FIG. 1 for receiving a powered drilling tool 200 and an elastic member 162 for capturing the powered drilling tool 200 within the cavity receptacle 152. The cavity receptacle is best seen in FIG. 1, the powered drilling tool in FIGS. 2 and 3 of the drawings, and the elastic member 162 in FIG. 1. The powered drilling tool 200 is preferably of the compressed air driven turbine type available from several suppliers in the surgical instrument and industrial equipment markets, but can be any type of transducer device, including vibration, ultrasound and laser devices where suitable. Pressurized air is supplied to the powered drilling tool 200 by way of a hose member 202 also shown in FIG. 2 of the drawings.

Returning now to the upper movably disposed connecting bar 112, FIG. 1 indicates the bar 112 to be supported from a pair of sliding blocks 120 and 121 which move along a pair of cylindrical guide members 124 and 125 mounted in upper and lower ends of the upright standards 106 and 108, i.e., in the foot member 154 at the lower end of the standard 106. Positioning of the sliding blocks 120 and 121 along the guide members 124 and 125 is controlled by a fourth threaded lead screw member 127 which engages the sliding block 120 in the manner described for the lead screws 128 and 138 in FIG. 1. A bell crank member 126 is used for rotating the lead screw 127 and controlling the position of the connecting bar 112 along the upright standards 106 and 108 and the guide members 124 and 125. A flexible cord, pulley, and counterweight elements 144, 146 and 147, respectively are shown connected to the block 121 in FIG. 1 to provide weight balancing of the way member 122 and the associated elements and to provide for minimum effort movement of the bell crank 126 in changing elevation of the powered drilling tool 200.

The optional support leg member 148 in FIG. 1 is provided with a captured ball type of movable foot 158 in order to track movement of the way member 114 along the connecting bar 112. The support leg member 148 is also provided with height adjustment capability which is locked into a selected position by means of the threaded screw members 160. The interface of the way member 114 with the connecting bar 112 is preferably arranged to employ low friction pads (not shown) of fluorinated hydrocarbon or similar material in order that lateral movement of the way member be possible with minimum effort and without damage to the faces of the connecting bar 112. Since these pads also resist a tendency of the way member 114 and associated elements to rotate about the bar 112 from their own mass, the pad members are preferably made large and rigid in nature.

By way of movement along the four described sets of guide members 124–125, 134, and 140, the powered drilling tool, 200, received in the cavity receptacle 152 can be positioned at substantially any point within a working field bounded by the upright standards 106 and 108, the table 102, and the support leg member 148. During such positioning of the powered drilling tool 200, the angle of disposure of the drilling tool cutter bit 206 can be maintained constant with respect to the plane of the table 102. In any of the possible positions of the powered drilling tool, axial movement of the cutter bit 206 is provided by motion along the guide member 140, and is precisely controllable as to axial position by way of the threaded lead screw 138. In addition to the aforementioned pads located at the interface of the members 112 and 114, movement along the guide members 124–125, 134, and 140 is preferably facilitated through the use of metal low friction bearings made from, for example, bronze or by linear ball bearing members disposed between the slide and moveable members or by other low friction low wear arrangements known in the mechanical arts.

During use of the FIG. 1 apparatus to access a spinal vertebra bone biopsy sample, the test subject, which is preferably from the aforementioned rhesus monkey primate family, but can be any vertebrate animal or human test subject, is anteriorly reposed, that is, located in a face down position, across the table 102 with the spinal axis substantially parallel with the connecting bar 110. Preferably, the test subject is held in a surgical cradle of the type shown at 104, and is, of course, anesthesized, sedated, or tranquilized, according to normal surgical art procedures.

Figure 2:
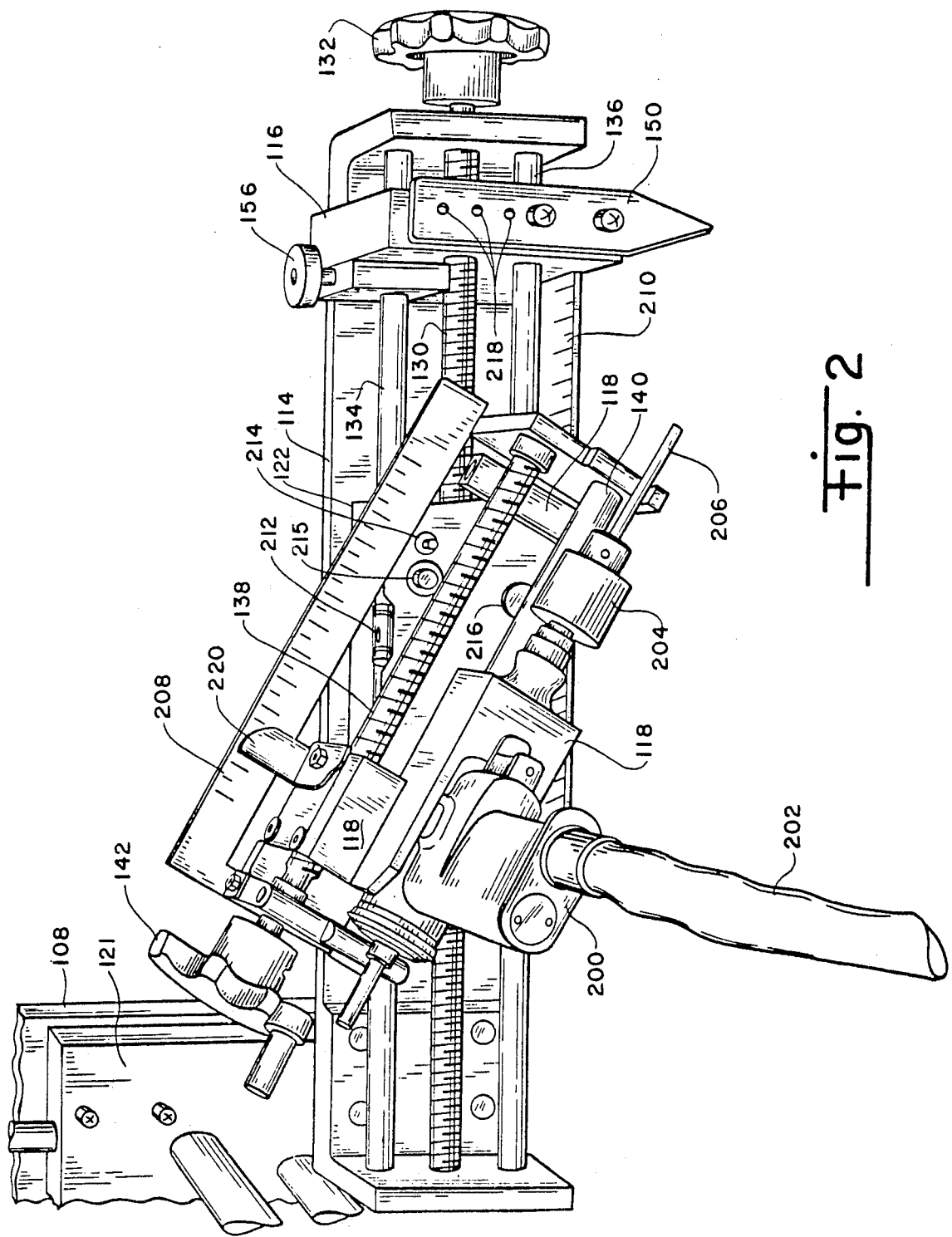
FIG. 2 is a closer, slightly elevated view of the sample obtaining portion of the FIG. 1 apparatus.

Additional details of the FIG. 1 sample accessing apparatus are shown in FIG. 2 of the drawings. In FIG. 2, several of the elements described in the FIG. 1 drawings are shown from a different viewing angle, but are nevertheless designated by the same identification number used above in the FIG. 1 description. The elements shown in FIG. 2 include the powered drilling tool 200, the pressurized fluid hose 202, and cutter bit 206 mentioned above in connection with FIG. 1. FIG. 2 elements not completely described above include the powered drilling tool adjustable chuck 204, and a measurement scale and pointer 208 and 220, which serve to precisely define the axial position of the powered drilling tool 200 and the trephine cutter bit 206. Also shown in FIG. 2 are a second measurement scale 210 which serves to indicate position of the tool platform member 122 with respect to the way member 114 and the index assembly 116. As shown in FIG. 2, the sample accessing apparatus also includes a bubble leveling member 212 for the tool platform member 122, a tool platform pivot member 214, a tool carriage member locking screw 216, a ninety-degree stop 215 for the tool carriage member 118 and a set of multiple position mounting holes 218 for the index pointer 150.

During use of the sample accessing apparatus as shown in the FIG. 2 view thereof, it is contemplated that the way member 114 will be disposed across the spinal axis of the test subject, with the index pointer 150 carefully aligned with and directly touching the rearward extending spinal process of the test subject—that is, just touching the skin tissue of the test subject exterior of the rearward directed spinal process. Alignment of the pointer 150 can be aided if desired by using a spinal process flag marker, e.g., a hypodermic needle, tapped lightly into one of the rearward process bones prior to positioning the pointer 150 as is shown at 305 in FIG. 3. Such flag markers are of great assistance if the FIG. 3 access is attempted by upguided hand techniques but are usually unnecessary with the FIGS. 1–3 apparatus. With the pointer 150 thusly aligned with the test subject's rearward process, the tool platform member 122 is positioned using the measurement scale 102 in accordance with a trigonometric calculation described below in order to provide the desired 30° angular access of the trephine cutter bit 206 with the vertebral centrum portion of a selected vertebra in the test subject spinal column. The depth of penetration of the trephine cutter bit 206 through the test subject vertebra is controlled by way of the scale 208 commencing from a point of first vertebra contact; a penetration depth in the order of 2 cm is appropriate in the case of the rhesus monkey test subject. The appropriate penetration depth is established for each test subject by way of a radiographic process described below.

Figure 3:
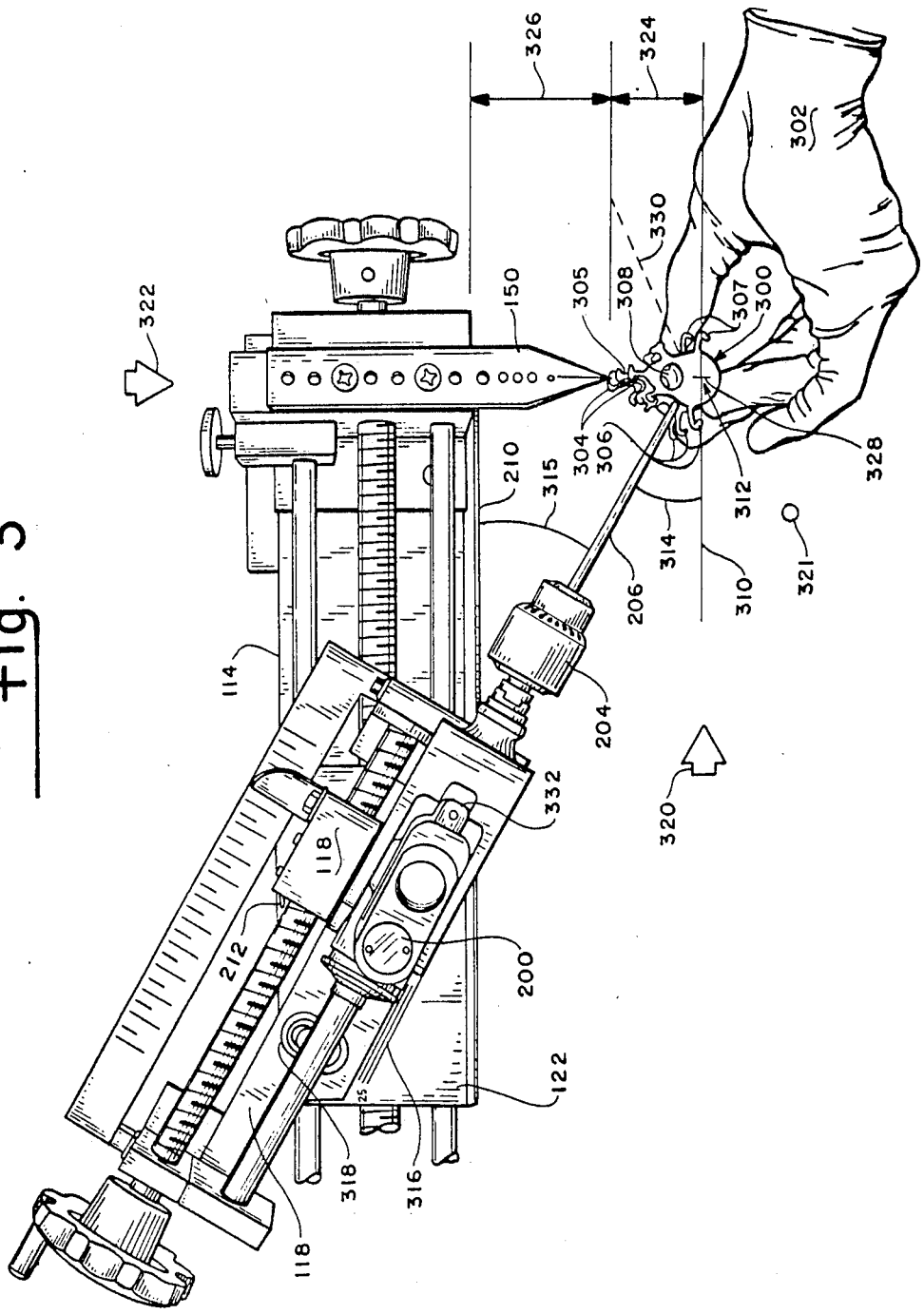
FIG. 3 shows a frontal perspective portion of the FIG. 2 apparatus and a spinal vertebra mobel in sample accessing relative position.

FIG. 3 in the drawings shows an additional straight-on view of the FIG. 1 and FIG. 2 sample accessing apparatus and includes several details not visible in the FIGS. 1 and 2 drawings. FIG. 2. also shows the preferred alignment positions of the pointer 150 and the trephine cutter bit 206 with a model representation of a spinal vertebra 300. Several of the major elements identified in FIGS. 1 and 2 of the drawings are numbered with the 100 series and 200 series identification numbers in FIG. 3 for consistent reference purposes. Elements first introduced in FIG. 3 are identified with 300 series numbers in keeping with the practice used in FIG. 2.

By way of the representative spinal vertebra 300 in FIG. 3, the desired area of vertebral centrum biopsy sample location can be understood and the functioning of the FIG. 1 and FIG. 2 apparatus in accessing the vertebra centrum 312 can be appreciated. The representative spinal vertebra model 300 includes right and left lateral process elements 306 and 307, the rearward directed process elements 304, and the spinal cord cavity 308. Since the FIG. 3 vertebra is fabricated from radiographic views of a living test specimen, only these major details of an actual vertebra are shown.

In addition to the spinal vertebra detail shown in FIG. 3, the location of a radial plane lateral to the spinal vertebra 300 is indicated at 310 in FIG. 3; this plane is located to pass through the centroid of the vertebra centrum 312 and actually extends toward and away from a viewer from the plane line 310. This plane is considered to be radial in nature in the sense that it encompasses radii drawn outward from the centrum centroid. The intersection of the lateral plane 310 with the centrum centroid 328 may be considered to define the spinal axis of the test subject. In the FIG. 3 view, of course, the test subject is also presumed to be disposed horizontally in an anteriorly reposed or prone position with feet above the plane of FIG. 3 and head below the plane of FIG. 3, for example.

In obtaining a trephine bone biopsy sample from a living test specimen, it is, of course, desirable to avoid injury to the test specimen by obtaining the bone biopsy sample precisely in the manner indicated in FIG. 3. The critical portions of the FIG. 3 relationship include having the trephine cutter bit 206 avoid any entrance into the spinal cord cavity 308, avoid contact, including root area contact, with the lateral processes 306 and 307, avoid significant emergence from the centroid region 312 on the right-hand side of the vertebra 300, and of course, avoid contact with the aorta or venus blood circulation members which are located immediately below the centrum 312 in FIG. 3 in a living test specimen. The FIG. 3 indicated alignment of the test specimen and sample accessing apparatus achieve these desired goals.

In the preferred rhesus monkey test specimen the angle 314 between the trephine cutter bit and the lateral plane 310 is desirably arranged to be thirty degrees with an acceptable tolerance of plus or minus one degree. At this angle the cutter bit enters the centrum 312 above the left lateral processes 306 and emerges or reaches the point of emergence below the right lateral processes 307. The preferred thirty degree angle is indicated at 314 in FIG. 3. The angle 315 in FIG. 3 between the cutter bit 206 and the way member 214 is equal to the angle 314 according to the geometric principle that a diagonal forms equal alternate angles at each of two parallel planes. The sample accessing apparatus is provided with an angular measurement scale 316 which may, for example, cover the range between 25 and 35 degrees of angle measure where interest is confined to the rhesus monkey and similar test specimens. A circumferentially disposed slot 318 and set screw received therein are used to hold the tool carriage member 118 in the selected angular position; these elements are aided by the previously mentioned locking screw 216.

The trephine cutter bit 206 is preferably selected to provide a centrum sample which is in the order of three millimeters in diameter. The outer diameter of the cutter bit 206 is, of course, somewhat larger than this 3 mm, but is nevertheless safely accommodated within the vertebra centrum 312 without injury to the test subject by way of the precise positioning possible with the disclosed apparatus. Samples smaller in diameter than this three millimeters are also feasible but are found to be somewhat more difficult to remove from the interior of the trephine cutter bit without incurring compression or other physical damage.

Removal of plural samples of the type indicated in FIG. 3 from a single test subject has been found to be especially useful and to provide no danger to the test subject. Such plural samples can be removed from different vertebrae by index movement of the way member 114 along the connecting bar 112 using a scale (not shown) together with dimensions obtained by radiographic examination. Plural samples can also be removed from a single vertebra with caution and due consideration for the resulting structural weakening of the sampled vertebra.

An especially useful application of the accessing apparatus herein disclosed involves removal of a sample in the manner indicated in FIG. 3 prior to exposing the test subject to a period of bone changing stress such as weightlessness, limited activity, or other conditions, then removing a second sample from the opposite side of the test specimen—a sample taken along the path indicated at 330 in FIG. 3, following the stress period and in order to observe the bone regrowth region where the first and second sample paths intersect. This bone regrowth area which lies in the first sample path and at the centrum center is of special technical interest, since the conditions under which this regrowth occurred can be controlled and vital stain techniques such as tetracycline bone labeling can be employed to precisely identify different portions such as layers in the region of intersection of the two sample paths.

For study purposes, it is usually preferable for the vertebra sample to extend fully through the vertebra centrum 312 in order that full samples of both the outermost and innermost bone material be achieved. Notwithstanding this desirability of a full diameter sample, it is also desirable that the trephine cutter bit 206 not extend into the lateral processes 307 or disassociated these lateral processes from the centrum portion 312—the accuracy and precision of the sample attainable with the presently disclosed apparatus makes such full diameter and desirably located samples possible.

As indicated above, location of the trephine cutter bit 206 in an angular plane having an angle 314 of substantially thirty degrees, with the lateral plane 310 is desirable for achieving spinal centrum bone biopsy samples in the rhesus monkey test subject. In order to establish this thirty degree angular approach in the rhesus monkey and to establish similar angles for other specimen types from the canine, feline, bovine, or other animal species, for example, it is desirable to use a radiographic and trigonometric calculation sequence.

Radiographic mapping of the spinal lumbar region of a test subject may be accomplished using conventional orthogonal radiograph views as represented by the arrows 320, 321, and 322 in FIG. 3; the representation at 321 indicating the tail end of an arrow directed into the plane of the FIG. 3 drawing. Radiographs of this type may be obtained using x-ray radiation, nuclear isotope radiation, radioactive tracer and scintillation scanning, and to a more limited degree, nuclear magnetic resonance scanning, sonograph and other procedures known in bone mapping.

Trigonometric calculations have been found desirable for determining distances to be measured along the scale 210 and thereby locating the tool platform member 122 and the trephine cutter bit 206 with respect to the index pointer 150 and the test subject. With the angle 315 having a value of 30 degrees, knowledge of the distances 324 and 326 in FIG. 3 enables calculation of distances along the scale 210 by way of the trigonometric tangent function. One of these distances, the distance 324 between the centroid of the spinal centrum 312 and the exterior of the skin tissue covering the spinal processes 304 is measurable from the radiographic mapping procedure. The measured distance 324 is, however, preferably corrected for the slight magnification present in most radiographic techniques. With the distance 324 determined and the distance 326 being measurable or assignable, according to the length of the index pointer 150, the distance along the measurement scale 210 is found by dividing the summation of distances 326 and 324 by the tangent (0.577) of the 30 degree angle 315. Distances along the measurement scale 210 are measured to a pointer, not shown, which is attached to the tool platform member 122; this pointer should preferably indicate distances along the scale 210 ending at the intersection of the scale 210 with the axis of the trephine cutter bit 206. Other locations of a tool platforms pointer can, of course, be accommodated through appropriate mathematical corrections and angles other than the rhesus monkey preferred thirty degrees can be readily accommodated by appropriate mathematical changes. Automatic calculation means such as an analog or digital computer or appropriate marking on the scale 210 relating to the distances 324 and 326 could also be included in the apparatus if desired.

As indicated above, the powered drilling tool 200 is preferably embodied as a pneumatically operated drill such as the Mini-Driver drill sold by 3M Company of St. Paul, Minn., or an equivalent device. Electrically powered, hand powered, hydraulically powered, or other types of drills could of course, be used in the FIG. 1 to FIG. 3 apparatus. The trigger 332 of the powered drilling tool 200 can be operated manually or arranged for remote mechanical operation or permanent retention in the ON position as desired. The adjustable chuck 204 allows use of different sized or different types of cutter tools in lieu of the trephine cutter bit 206, as needed or the substitution of non-cutting tools such as pointers and probing electrodes in alternate uses of the FIG. 1 through FIG. 3 apparatus. The vertebra 300 in FIG. 3 is shown to be held by a human hand 302 for the purpose of illustrating the interrelationships described in FIG. 3; in actual use the vertebra would of course, be within the living test specimen or alternately, if from a deceased specimen, could be mounted in a vise, a plaster mold, or other such arrangements as are known in the biological arts.

The disclosed spinal biopsy trephine sample arrangement provides several advantages over apparatus and procedures used heretofore in axial skeleton bone studies. Previously for example, it has been common practice to extract such samples from the tibia or other limb bones of a test specimen because of the resulting ease of access, and the limited prospects for test specimen injury. Since the trabecular bone desired for sampling develops along the lines of greatest stress in a skeleton, and is well represented in the spinal vertebra, a spinal vertebra sample is considerd superior for many purposes over tibia or other peripheral limb bone samples.

The uncluttered field and simple structural elements of the present invention also offer desirable practical advantages in the logistics of bone biopsy. Frequently in obtaining bone samples, for example, there is need for x-ray equipment, lighting, several participating persons, and surgical procedure. Bone biopsy apparatus of the complexity shown in the above referenced U.S. Pat. No. 3,374,548, for example, would clearly increase the clutter and logistics problems attending such a procedure.

The described biopsy arrangement has also been found to be both rapid and convenient in application, thereby allowing the attainment of several samples such as samples from different vertebra of the same test subject in an optimum manner. Movement of the trephine cutter bit between first, second, and third sample locations in different vertebra in accordance with dimensions ascertained in a single radiographic mapping procedure, has been found feasible and safe using the disclosed apparatus and procedure. The described apparatus moreover enables use of vertebra centrum samples which were heretofore believed too dangerous and difficult to access. Previously, for example, in both scientific investigation and in human medicine practice, there has been great reluctance to penetrate the entire vertebral centrum area for fear of causing injury to the test subject, notwithstanding the desirability of the bone sample attained thereby. The precise radiographic knowledge and precise measurements achieved using the present apparatus effectively removes these barriers.

While the apparatus and method herein described constitute a preferred embodiment of the invention, it is to be undertood that the invention is not limited to this precise form of apparatus or method, and that changes may be made therein without departing from the scope of the invention, which is defined in the appended claims.

We claim:

1. Trephine biopsy apparatus comprising:

a planar surface member;

a first vertical upstanding support column assembly releasably attached to said planer surface member;

a second vertical upstanding support column assembly releasably attached to said planar surface member and disposed parallel to said first vertical upstanding support column assembly;

said vertical upstanding column assemblies each including a vertical upstanding support member and a vertical upstanding guide member;

a pair of vertically movable follower members each slidably received on one of said upstanding guide members;

a rotatable vertical lead screw member located in one of said upstanding support column assemblies, disposed parallel of said guide members and support member therein and threadably received in one of said vertically movable follower members;

a horizontally disposed transverse assembly suspended between said upstanding support column assemblies in connection with said vertical follower members and selectably positionable vertically along said column assembies by said vertical lead screw and threadably received follower members;

said transverse assembly including a rigid transverse structural member and a transverse lead screw member disposed parallel thereto;

a transverse movable follower member threadably received on said transverse lead screw member;

a horizontally disposed way assembly cantilever supported from said horizontally disposed transverse assembly in connection with said transverse lead screw member, said way assembly being orthogonal to said transverse assembly and parallel to said planar surface member;

said horizontally disposed way assembly including a plurality of horizontal guide members and a lead screw member disposed parallel thereto;

a tool platform member suspended on said horizontally disposed way assembly, including a follower portion slidably received on said way assembly horizontal guide members and treadably received on said way assembly lead screw member and movable along said horozontal guide members in said orthogonal plane;

said tool platform member including a sloped way assembly pivotally mounted thereon and disposable within predetermined angular limits with respect to said planar surface member, said sloped way assembly also having parallel disposed guide and lead screw members;

a tool carriage member mounted on said tool platform member way assembly, said carriage member including follower portions slidably received on said sloped way assembly guide member and threadably received on said sloped way assembly lead screw member, said carriage member being thereby movable along said sloped way assembly guide and lead screw members at said predetermined sloped angle with respect to said planar surface member;

a powered drilling tool received in said tool carriage member and including a rotationally driven trephine cutter bit driving member;

elongated cradle receptacle means disposed parallel to said transverse assembly on said planer surface member for retaining a horizontally reposed vertebrate test specimen in predetermined alignment with said trephine cutter bit driving member.

2. The apparatus of claim 1 further including third vertical upstanding column means movably supported on said planar surface member and attachable to said horizontally disposed way assembly distal of said transverse assembly for supporting the free end of said way assembly in predetermined elevation above said planar surface member.

* * * * *